US005688978A

United States Patent [19]

Lefebvre et al.

[11] Patent Number: 5,688,978

[45] Date of Patent: Nov. 18, 1997

[54] PREPARATION OF BETA HYDROXYLAKYL-TERMINALLY BRANCHED FATTY ACID AMIDES

[75] Inventors: Ginette Lefebvre, Bosc Roger en Roumois; Line Fiquet, Rouen, both of France

[73] Assignee: Witco Corporation, Greenwich, Conn.

[21] Appl. No.: 440,009

[22] Filed: May 12, 1995

Related U.S. Application Data

[62] Division of Ser. No. 167,773, Dec. 15, 1993, Pat. No. 5,439,615.

[51] Int. Cl.[6] .......... C07C 231/00

[52] U.S. Cl. .......... 554/69; 554/68; 554/66; 252/548

[58] Field of Search .......... 554/66, 68, 69; 252/548

[56] References Cited

U.S. PATENT DOCUMENTS

| | | |
|---|---|---|
| 4,559,227 | 12/1985 | Chandra et al. . |
| 4,654,163 | 3/1987 | Quack et al. . |
| 4,704,272 | 11/1987 | Oh et al. . |
| 4,728,457 | 3/1988 | Fieler et al. . |
| 4,741,855 | 5/1988 | Grote et al. . |
| 4,885,107 | 12/1989 | Wetzel . |
| 5,151,209 | 9/1992 | McCall et al. . |
| 5,151,210 | 9/1992 | Steuri et al. . |

FOREIGN PATENT DOCUMENTS

| | | | |
|---|---|---|---|
| 2427319 | 12/1975 | Germany | 554/66 |

*Primary Examiner*—Gary Geist
*Assistant Examiner*—Deborah D. Carr
*Attorney, Agent, or Firm*—Lockwood, Alex, FitzGibbon & Cummings

[57] ABSTRACT

New and improved thickeners for mixtures of one or more surface active agent include beta-hydroxyalkyl-terminally branched fatty acid amides. The new and improved thickeners achieve the same or better viscosity with lower amounts of mineral salts being required to be added. Concomitant benefits such as improved softening, lubricity, emulsifying and foam intensifying properties are also achieved. The thickeners and cleaner compositions containing them may also be prepared so that they do not contain nitrosamines, unlike prior art amide thickeners. A preferred thickener in accordance with the invention is 2-hydroxypropyl-isostearyl amide. A novel method for making the preferred thickener, so that it is substantially free of undesirable impurities is also provided.

1 Claim, 3 Drawing Sheets

PREPARATION OF BETA HYDROXYLAKYL-TERMINALLY BRANCHED FATTY ACID AMIDES

This is a divisional of application Ser. No. 08/167,773 filed Dec. 15, 1993, now U.S. Pat. No. 5,439,615.

BACKGROUND OF THE INVENTION

The present invention generally relates to fluid cleaning compositions containing water and one or more surfactants, soaps and/or detergents. More particularly, it relates to a new and improved thickening agent containing an amide useful for thickening liquid cleaner compositions.

Illustrative examples of cleaning compositions containing a mixture of at least one surface-active agent whose viscosity characteristics may need to be modified or increased may include cosmetics, such as shampoos, shower gels or creams, as well as, liquid detergents for use in the home, e.g., dishwashing liquids, bathroom and toilet cleaners and gels, and liquid laundry detergents, to name but a few. It may be desired to modify the viscosity of these liquids by increasing the viscosity to provide thicker or thickened liquids.

It is well known that surface-active agents in a dilute mixtures produce low viscosity formulations. Whenever the mixture has a low viscosity, contact with the surface on which it is used is often undesirably short, i.e., the cleaner runs or rolls off the surface. Moreover, since the product flows more easily, it has no time to react with the surface so that the user tends to use too much of the cleaner.

In order to solve this problem, many thickening agents have been added into cleaner compositions. Among them diethanolamides that are prepared with secondary amides. These materials contain high amounts of nitrosamines which is a serious drawback because it is well known that nitrosamines are carcinogenic. Copra diethanolamides have been extensively used for this purpose since they are in a liquid form and can be easily handled at room temperature, despite the fact that they contain nitrosamines. Moreover, copra diethanolamides do not provide high viscosity mixtures except at relatively high amide concentrations.

The use of palm, copra, stearin and olein monoisopropanolamides has also been suggested, because these amides generally do not contain nitrosamines since they are prepared from primary amines. However, these amides are solid at ambient or room temperatures and therefore are difficult to handle.

Furthermore, until recently, in order to obtain a cleaning mixture with a desirably high viscosity, it has been necessary to add a large quantity of mineral salt, such as sodium chloride or magnesium sulfate. For a given quantity of thickening amide, viscosity of the overall formulation increases to a maximum as mineral salts are added and then decreases. With the type of amides used, optimum viscosity can only be achieved with relatively high quantities of mineral salts (NaCl, $MgSO_4$). A major disadvantage associated with adding large amounts of mineral salts to the formulation is that the cleaner product is less stable at low temperature and less soft when used. These drawbacks are even greater when the mineral salt content is higher.

According to this invention, it is easy to prepare mixtures containing at least one surface-active agent, having a desirably high viscosity, having only a minimum quantity of mineral salts. More particularly, superior viscosity modification at lower salt concentrations is provided by using certain room temperature liquid amides as the thickening agent which do not contain nitrosamines.

SUMMARY OF THE INVENTION

A primary object of this invention is to provide a new and improved thickener for cleaner compositions comprising certain fatty acid amides derived from beta-hydroxyalkyl units and terminally-branched fatty acid units having a long hydrocarbon chain containing at least about 14 carbons in length. In accordance with the preferred embodiment, the new and improved amide thickener in accordance with this invention comprises a 2-hydroxypropyl-isostearyl amide.

It has been observed that in addition to its excellent viscosity, 2-hydroxypropyl-isostearyl amide has softening, lubrifying, emulsifying and foam-intensifying properties. Another advantage of 2-hydroxypropyl-isostearyl amide is that ambient temperature mixtures containing at least one surface-active agent can be formulated because the amide is a liquid and easy to handle at this temperature. It is therefore easy to introduce with surface active agents.

The preferred amide shown in structural formula (1) can be obtained by condensing isostearic acid and amino-1 propanol-2 (also called 2-hydroxypropylamine, monoisopropanolamine or MIPA). At 20° C. the product looks like a clear to slightly cloudy liquid which gets clearer between 30° and 40° C. The density of this amide, measured at 40° C. is equal to about 0.0904 and its viscosity at 40° C. is equal to about 320 mPa.s.

In addition, the invention relates to a thickening agent that can be used in mixtures containing at least one surface-active agent which is made up of at least one fatty acid amide characterized by the fact that it contains the amide given in structural formula (1). The thickening agent contains at least 90 weight % of the amide given in structural formula (1).

The thickening agent in this invention meets the following specifications:

| | |
|---|---|
| Visual at 25° C. | Clear to slightly cloudy liquid |
| Density at 40° C. | 0.900–0.908 |
| Viscosity at 40° C. | 310 to 330 Mpa · s |
| Color at 40° C. (measured in Gardner units) | ≦3 |
| Acidity (in mg KOH/g) | ≦3 |
| Free amine content (weight %) | ≦1 |
| Esteramide content (weight %) | ≦5 |
| Ph measured in a weight % solution in a water/isopropanol mixture (50/50 in volume) | 8 to 9 |
| Water content | ≦0.5 |

This invention also relates to thickened compositions comprising a liquid or pasty mixture containing at least one surface-active agent and an effective quantity of the thickening agent defined above. Other object and advantages provided by the present invention will become apparent from the following Detailed Description of the Preferred Embodiments, taken in conjunction with the Drawings, in which:

DETAILED DESCRIPTION OF THE INVENTION

Figure 1:
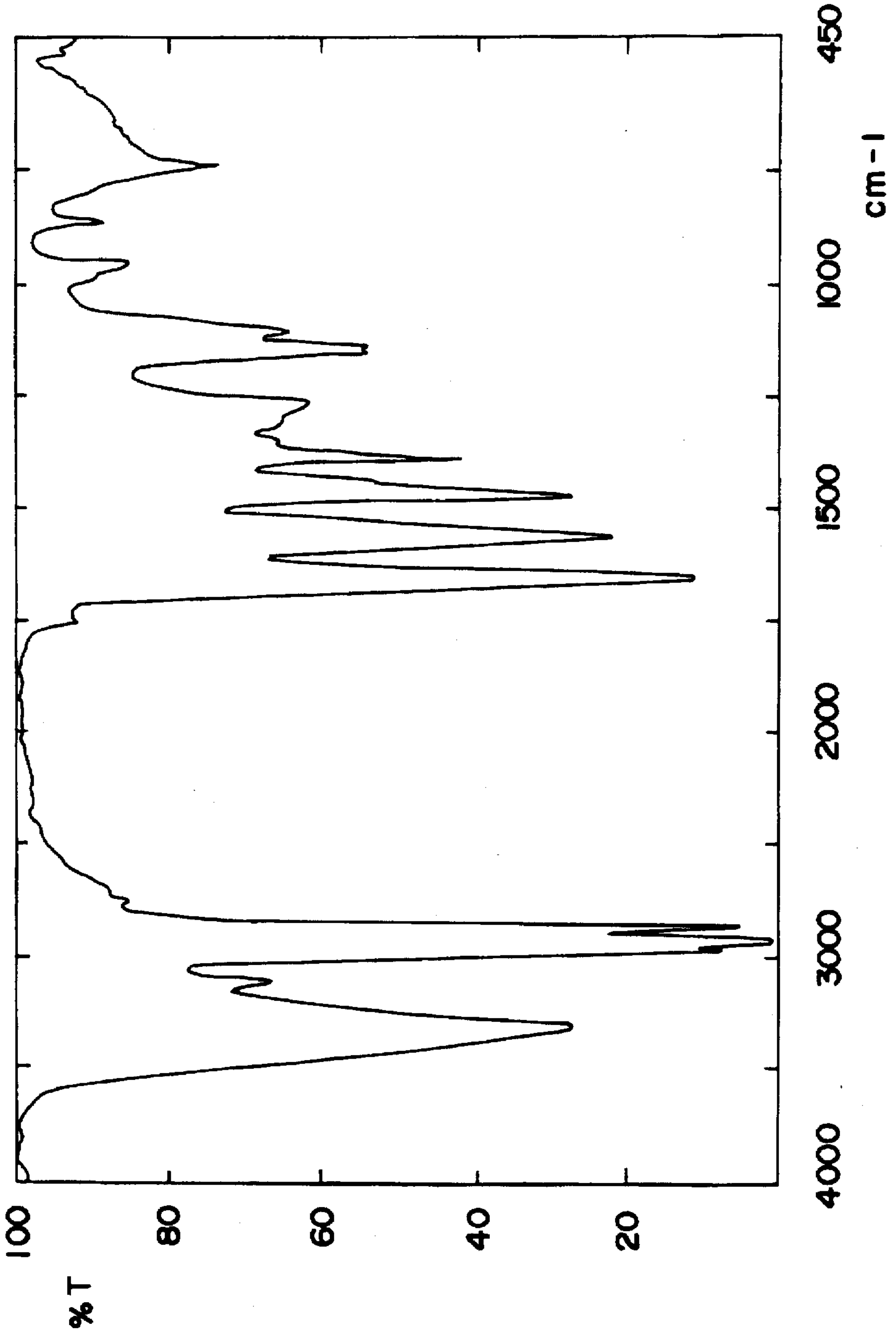
FIG. 1 is a copy of the Infra-Red Spectrum of the new and improved 2-hydroxypropyl-isostearyl amide thickener compound of the present invention.

According to the invention, the thickening agent is compatible with most surface-active agents and soaps. Surface-active agents can be selected from the following group in the case of this invention: anionic, cationic, zwitterionic and amphoteric surfactants and mixtures thereof, alkaline alkylamidosulfosuccinates, sodium, potassium or triethanolamine soaps, betaine and sulfobetaines, amphoteric surface-active agents derived from imidazoline, alkylpolyglycolethers, polyalcohols, polyethyleneglycol, and more particularly, sorbitol or ethoxyl sorbitol fatty esters.

More particularly, suitable anionic surfactants are water-soluble salts of $C_8$–$C_{22}$ alkyl benzene sulfonates, $C_8$–$C_{22}$ alkyl sulfates, $C_{10-18}$ alkyl polyethoxyether sulfates, $C_{8-24}$ paraffin sulfonates, alpha—$C_{12-24}$ olefin sulfonates, alpha-sulfonated $C_6$–$C_{20}$ fatty acids and their esters, $C_{10}$–$C_{18}$ alkyl glyceryl ether sulfonates, fatty acid monoglyceride sulfates and sulfonates, especially those prepared from coconut oil, $C_8$–$C_{12}$ alkylphenol polyethoxyether sulfates, 2-acyloxy—$C_9$–$C_{23}$ alkane-1-sulfonate, and beta-alkyloxy —$C_8$–$C_{20}$ alkane sulfonates.

Preferably, the anionic surfactant is selected from alkali metal, alkaline earth metal, ammonium, and alkanolammonium salts of alkyl sulfates, alkyl ethoxy sulfates, alkyl benzene sulfonates and mixtures thereof.

The alkyl sulfate component is preferably a primary alkyl sulfate in which the alkyl group contains about 10–16 carbon atoms, more preferably an average of 12–14 carbon atoms. The alkyl group may be linear or branched in configuration. $C_{10}$–$C_{16}$ alcohols, derived from natural fats or Ziegler olefin build-up or OXO synthesis, from suitable sources for the alkyl group. Examples of synthetically derived materials include Dobanol 23 (RTM) sold by Shell Chemicals (UK) Ltd., Ethyl 24 sold by the Ethyl Corporation, a blend of $C_{13}$–$C_{15}$ alcohols in the ratio 67% $C_{13}$, 33% $C_{15}$ sold under the trade name Lutensol by BASF GmbH and Synperonic (RTM) by ICI Ltd., and Lial 125 sold by Liquichimica Italiana. Examples of naturally occurring materials from which the alcohols can be derived are coconut oil and palm kernal oil and the corresponding fatty acids.

For the purposes of the present invention any alkali metal, alkaline earth metal, ammonium or substituted ammonium cation can be used in association with the alkyl sulfate. In particular, the alkyl sulfate can be associated with a source of magnesium ions either introduced as the oxide or hydroxide to neutralize the acid, or added to the composition as a water soluble salt.

Alkyl benzene sulfonates preferred for use in compositions of the present invention are those in which the alkyl group, which is substantially linear, contains about 10–16 carbon atoms, preferably about 11–13 carbon atoms, a material with an average chain length of 11.8 being most preferred. An alkylbenzene sulfonate content of from about 10% to about 28% by weight of the composition is generally suitable. In a preferred aspect of the invention an alkylbenzene sulfonate content of from 13% to 17% by weight is used.

The alkyl ethoxy sulfate surfactant component preferably comprises a primary alkyl ethoxy sulfate derived from the condensation product of a $C_{10}$–$C_{16}$ alcohol with an average of up to 6 ethylene oxide groups. The $C_{10}$–$C_{16}$ alcohol itself can be obtained from any of the sources previously described for the alkyl sulfate component. It has, however, been found preferable to use alkyl sulfate and alkyl ether sulfate in which the carbon chain length distributions are the same. $C_{12}$–$C_{13}$ alkyl ether sulfates are preferred.

Conventional ethoxylation processes result in a distribution of individual ethyoxylates ranging from 1 to about 10 ethoxy groups per mole of alcohol, so that the desired average can be obtained in a variety of ways. Blends can be made of material having different degrees of ethoxylation and/or different ethoxylate distributions arising from the specific ethoxylation techniques employed and subsequent processing steps such as distillation. For example, it has been found that approximately equivalent sudsing to that given by a blend of alkyl sulfate and alkyl triethoxy ether sulfate can be obtained by reducing the level of alkyl sulfate and using an alkyl ether sulfate with an average of approximately two ethoxy groups per mole of alcohol. In preferred compositions in accordance with the present invention the average degree of ethoxylation is from about 0.5 to about 4, more preferably from about 0.8 to about 2.0.

Cationic detergents include those having the formula $R\text{-}N(R^2)_3(+)X(-)$ wherein R is an alkyl chain containing from about 8 to about 20 carbon atoms, each $R^2$ is selected from alkyl and alkanol groups containing from 1 to 4 carbon atoms and benzyl groups, there being normally no more than one benzyl group and two $R^2$ groups can be joined by either a carbon-carbon ether, or imino linkage to form a ring structure, and X represents a halogen atom, sulfate group, nitrate group or other pseudohalogen group, nitrate group or other pseudohalogen group. Specific examples are coconut alkyl trimethyl ammonium chloride, dodecyldimethyl benzyl bromide and dodecyl methyl morpholino chloride.

Zwitterionic synthetic detergents can be broadly described as derivatives of aliphatic quaternary ammonium, phosphonium, and sulfonium compounts, in which the aliphatic radical may be straight chain or branched, and wherein one of the aliphatic substituents contains from about 8 to 18 carbon atoms and one contains an anionic water solubilizing group, e.g., carboxy, sulfo, sulfato, phosphato, or phosphono. Examples of compounds falling within this definition are 3-(N,N-dimethyl-N-hexadecylammonio) propane-1-sulfonate and 3-(N,N-dimethyl-N-hexadecylammonio)-2-hydroxypropane-1-sulfonate.

Amphoteric synthetic detergents can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphone. Examples of compounds falling within this definition are sodium-3-dodecylaminopropionate and sodium-3-dodecylaminopropane sulfonate.

Other suitable surfactants herein are the long chain tertiary amine oxides of general formula:

$$R_1R_2R_3N{\rightarrow}O^-$$

wherein $R_1$ represents alkyl, alkenyl or monohydroxyalkyl radical of from 8 to 18 carbon atoms optionally containing up to 10 ethylene oxide moieties or a glyceryl moiety, and $R_2$ and $R_3$ represents alkyl of from 1 to 3 carbon atoms optionally substituted with a hydroxy group, e.g., methyl, ethyl, propyl, hydroxyl ethyl, or hydroxypropyl radicals. Examples includes dimethyldodecylamine oxide, oleyldi(2-hydroxyethyl)amine oxide, dimethyldecylamine oxide, 3,6, 9-trioxaheptadecylamine oxide, 2-dodecoxyethyldimethylamine oxide, 3-dodecoxy-2-hydroxypropyl-di-(3-hydroxypropyl)-amine oxide, dimethylhexadecylamine oxide. The amine oxide surfactants are generally referred to as semi-polar although in acidic to neutral media they behave akin to cationic surfactants.

According to the invention, the mixtures contain certain quantities of thickening agents that change depending on the type and the quantity of surface-active agent used and on the use of the mixture. These quantities vary between 0.1 and 2.5 weight & compared to the total weight of the mixture, preferably between 0.5 and 1.5%.

Mixtures thickened as per the invention, containing amides, also contain a mineral salt, a chloride, an alkaline-earth sulfate and more particularly sodium chloride or magnesium sulfate; the quantity of sodium chloride or magnesium sulfate required to obtain a given viscosity with a determinate quantity of amide can be reduced by using the amide from structural formula (1) as an essential constituent of the thickening agent; in practice, the quantity of sodium chloride or magnesium sulfate is therefore chosen so as to optimize viscosity according to the quantity of amide from structural formula (1) present in the mixture.

According to the invention, the mixture contains, for example, between 0.25 and 10 weight % of sodium chloride for a quantity or monoisopropanolamide isostearic acid ranging between 0.1 and2.5%; preferably, it contains between 0.75 and 1.75 weight % of NaCl for 0.5 to 1% of amide from structural formula (1).

According to the invention, the mixture can be used in a shampoo, a cream, a shower gel, a liquid soap or a liquid detergent for cleaning dishes, WV's, tiles.

Monoisopropanolamide isostearic acid can be prepared by reacting isostearic acid with monoisopropanolamine, through any known amide preparation process. A process through which a stoichiometric quantity or a slight excess of isopropanolamine is reacted with isostearic acid in the presence of phosphoric acid as a catalyst is preferred. However, depending upon the process used, a product can be obtained with too high a colored value (a coloring in Gardner units, greater than 5) with too high a content of esteramides, obtained as a secondary product, as well as, too high a content of free amines. Such a product when used with the amide from structural formula (1) may be problematic, as an appropriate thickening agent in mixtures.

According to the invention, a product with a coloring of 5 (maximum) in Gardner units, a content of 5 weight % (maximum) of esteramides and a content of 1 weight % (Maximum) of free amines can be obtained through the thickening agent preparation process described hereafter.

According to this process:

(a) isostearic acid is introduced in a reaction vessel through which an inert gas current is passed and heated at a temperature ranging from 40° to 70° C.;

(b) in this reaction vessel, an anti-oxidizing agent is then added and mixed for 0.5 to 2 hours;

(c) monoisopropanolamine is gradually introduced into the reaction vessel and temperature is increased until it reaches 90° to 110° C. This temperature is maintained by regulating monoisopropanolamine introduction flow until 1.00 and 1.10 times the number of acid moles has been introduced in the reaction vessel at step (a);

(d) the temperature is maintained and then phosphoric acid (between 2 and 5 parts in weight for 10,000 parts in weight of acid placed in the reaction vessel in step (a) is slowly introduced into the reaction vessel and heated until temperature reaches 145° to 170° C.;

(e) temperature is maintained until the acid is lower than 5 (mg KOH/g);

(f) when acid index is lower than 5, a second quantity of anti-oxidizing agent is added. A low pressure of 4.0 to $1.9\times10^3$ Pa is established by maintaining the inert gas atmosphere in order to eliminate excess amine;

(g) then, temperature is reduced to under 75° C. by maintaining the inert gas atmosphere and the mixture is allowed to return to room temperature.

The examples given hereafter are illustrations and in no way limitations and will allow permit those skilled in this art to better understand the invention.

DESCRIPTION OF THE PREFERRED EMBODIMENTS

EXAMPLE 1

Preparation of a 2-Hydroxypropyl-isostearylamide Thickener

The following components are used (quantities are given in grams):

| | |
|---|---|
| Isostearic acid | 668 |
| Monoisopropanolamine | 186 |
| Phosphoric acid at 85% | 0.24 |
| 2.6-di-tert-butyl-p-cresol (anti-oxidizing agent) | 1.92 |

A 1 liter reaction vessel is purged with nitrogen and the entire amount of isostearic acid is introduced. The acid is heated at a temperature ranging between 60 and 70° C. under a nitrogen flow of 0.41/h. Thereafter, half of the anti-oxidizing agent is added and maintained under agitation for one hour.

The monoisopropanolamine (MIPA) (2-hydroxypropylamine) is added in a thin stream. The reaction is exothermic and the temperature of the mixture increases. It is allowed to reach 100° C. so as to liquefy the reaction mixture and maintained at 100° C. by regulating the flow of MIPA.

After introducing MIPA, phosphoric acid is slowly introduced at 100° C. Nitrogen flow is doubled and the mixture is heated to 155°–160° C.

This temperature is maintained during the entire reaction until the acid index (in mg KOH/g) is lower than 5. The evolution of reaction is controlled by sampling it every one and a half hours. Acid index as well as alkalinity index are checked. The alkalinity index expressed in mg KOH/g must always be 10 points above the acid index. If it is not the case, the alkalinity index is adjusted by adding MIPA.

During the reaction, the nitrogen flow is gradually increased so that at the end of the reaction it reaches ten times the initial flow use date at the time the isostearic acid is heated. Therefore, the water formed is more easily drained. When the acid index is under 5 (mg KOH/g), the second half of the anti-oxidizing agent is added.

A pressure of 2.66 c $10_3$ Pa is set in the reaction vessel under a nitrogen flow of 4.3 liters/hour in order to eliminate excess MIPA through distillation. Distillation temperature of amine is very important because for higher temperatures, a product with too many esteramides would then be obtained. Low pressure is maintained until the alkalinity index is under 0.1 meq/g.

Finally, the reaction mixture is cooled down to 60° C. under a nitrogen flow of 0.91/h and then allowed to come back to ambient temperature.

With a 93% yield compared to the raw materials used, we thus obtain a thickening agent that satisfies the following specifications:

| | |
|---|---|
| Visual at 25° C. | Clear to slightly |
| cloudy liquid | |
| Color in Gardner units (%) | 4.5 |
| Acidity (mg KOH/g) | 4.2 |
| Free amine content (weight %) | 0.8 |
| Esteramide content (weight %) | 4.1 |
| Water content | 0.05 |
| Crystallization point (°C.) | 10 |
| pH in a 1% solution in a water/isopropanol mixture 50/50 in volume | 10 |
| Viscosity at 40° C. (mPa · s) | 8.8 |
| Density at 40° C. | 0.904 |

(%) Measurement is taken by comparing coloring disks in normal Gardner units from 1 to 18.

The infra-red spectrum of the compound thus obtained is given in FIG. 1, wherein wavelengths in $cm^{-1}$ are given on the x-axis and the transmission percentage on the y-axis. This spectrum confirms the fact that the product obtained is essentially made up of 2-hydroxypropyl-isostearyl amide.

EXAMPLE 2

Shampoo Preparation

A shampoo containing variable quantities of sodium chloride has been prepared. It has the following formulation (in weight %):

| | |
|---|---|
| Surface-active agents with sulfosuccinates acids sold on the market as "EMCOL 1484" by "WITCO" | 15 |
| Surface-active agents with sodium alkylethersulfates sold on the market as "NEOPON LOS/NF" by "WITCO" | 20 |
| Thickening agent | 1 |
| Sodium chloride | 1 to 10 |
| Water (balance) | 100 |

The thickening agent used is either the thickening agent of the invention obtained by the following Example 1, or, as a comparison, palm monoisopropanolamide sold as "WITCAMIDE PPA" by the WITCO Corporation and copra monoisopropanolamide sold as "WITCAMIDE CPA" by the WITCO Corporation.

Viscosity of the various formulations obtained was measured at 20° C. with a "Brookfield RVT" viscosimeter. The results of these measurements are given in FIG. 2. The percentage of sodium chloride is given on the x-axis and the viscosity measured at 20° C. in mPa.s, on the y-axis. Curve (a) corresponds to the thickening agent of this invention. Curve (b) shows the results obtained with the WITCAMIDE PPA and curve (c) with WITCAMIDE CPA.

Figure 2:
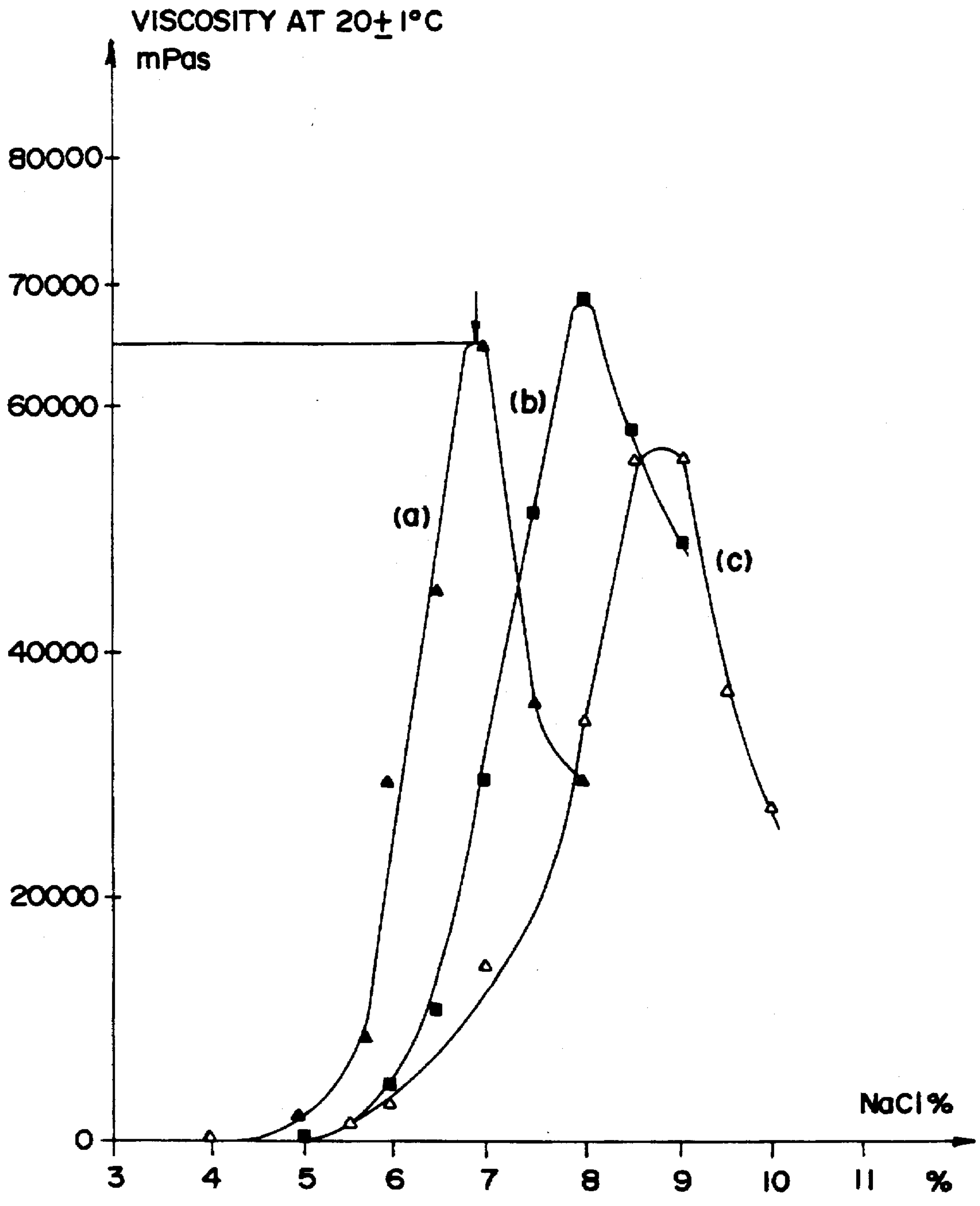
FIG. 2 is a graphical illustration showing the thickening ability of the thickener of the present invention, curve (a), compared to prior art compounds palm monoisopropanolamide, curve (b), and copra monoisopropanolamide, curve (c), shown in terms of viscosity, as measured at 20° C. in a Brookfield RVT Viscosimeter, as a function of NaCl mineral salt content.

FIG. 2 shows that a maximum viscosity obtained with the thickening agent of the invention is substantially similar to the viscosity achieved with the WITCAMIDE CPA and PPA prior art thickeners. A comparison of FIG. 2 results illustrates that for a given viscosity value, the viscosity was achieved using a smaller quantity of NaCl with the thickening agent of the invention, curve (a).

The cloud point of the above mixture containing WITCAMIDE CPA and WITCAMIDE PPA was measured as well as that for the thickening agent of the invention at a NaCl content of 7% and 8%. The results are given in Table 1 hereunder.

TABLE 1

| Thickeninq Agent | NaCl Content | Cloud Point °-C. |
|---|---|---|
| WITCAMIDE CPA | 7% | -4 |
| | 8% | -4 |
| WITCAMIDE PPA | 7% | -2 |
| | 8% | -2 |
| Thickening agent according to Example 1 | 7% | -7 |
| | 8% | -7 |

Therefore, the cloud point is clearly lower with the thickening agent from Example i rather than with WITCAMIDE PPA and CPA. Moreover, for the mixtures containing WITCAMIDE PPA and CPA, it has been observed that crystals have formed as it ages; with the thickening agent of the invention, this phenomena does not occur.

EXAMPLE 3

Preparation of a Dishwashing Liquid

A detergent dishwashing liquid containing 10% active ingredient was prepared with the following formulation (in weight %):

| | |
|---|---|
| Surface-active agents with p-alkylbenzene sodium sulfonate sold on the market as "SULFRAMINE 1230" by "WITCO" | 23.8 |
| Surface-active agents with alkylether sodium sulfate sold as "NEOPON LOS/NF" by "WITCO" | 10.2 |
| Thickening agent | 0.05 and 1 |
| Sodium chloride | 0.5 to 3 |
| City supply water (balance) | 100 |

The thickening agent used was either the preferred 2-hydroxypropyl-isostearyl amide of Example 1, copra diethanolamide, or copra monoisopropanolamide sold as WITCAMIDE CPA by WITCO Corporation.

Viscosity at 20° C.±1° C. was measured in mPa.s with the help of the Brookfield RVT viscosimeter.

Immediate foaming power has been measured in foam ml and after 5 minutes with a 0.1% solution of dry matter from city water formulations.

Cloud point in °C. has been determined and the appearance of the detergent obtained at 20° C. has been observed.

Figure 3:
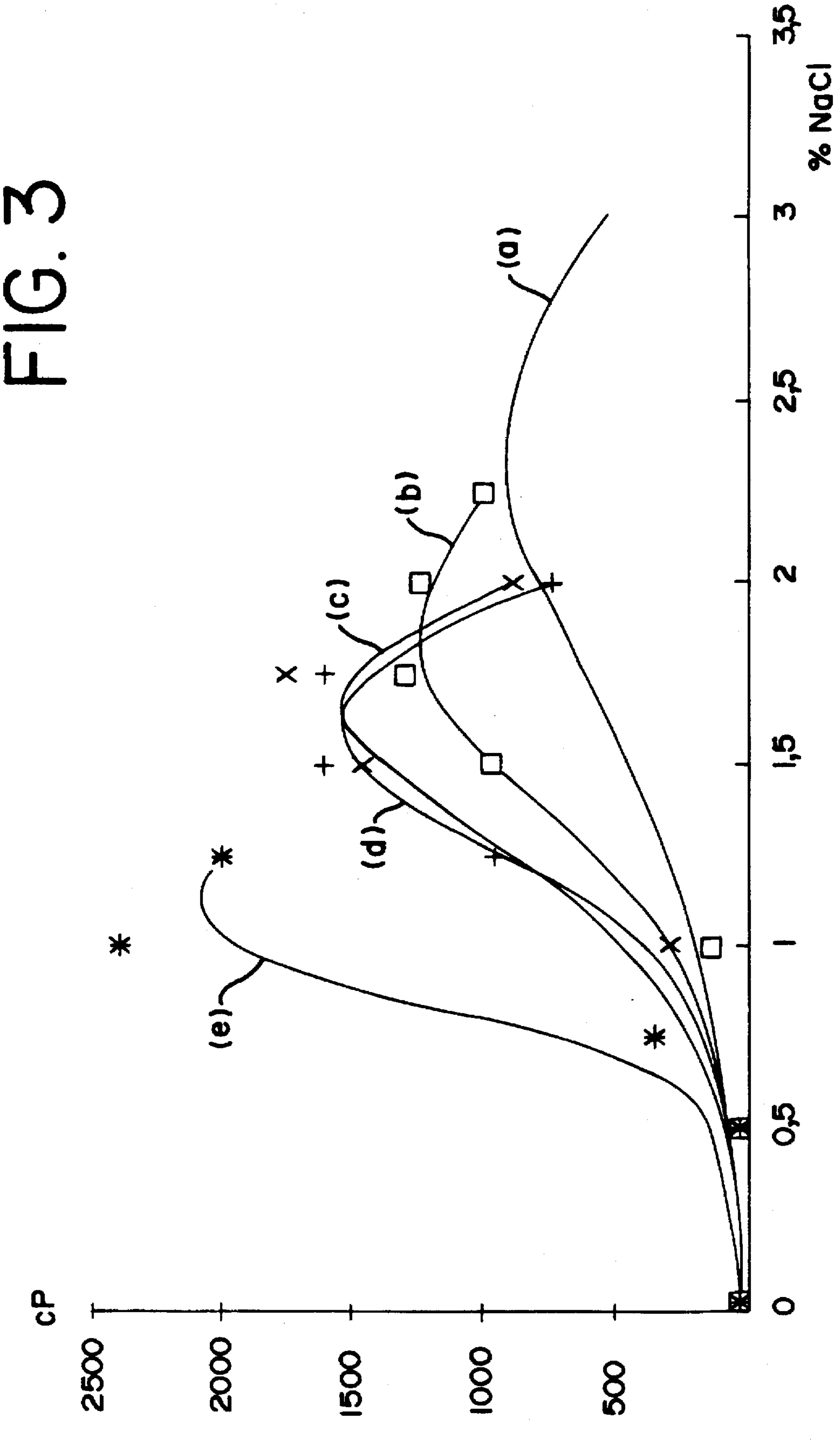
FIG. 3 is a graphical plot showing viscosity, as measured at 20° C. in a Brookfield RVT Viscosimeter, as a function of NaCl mineral salt content for a composition without thickener, curve (a); with 0.5% copra diethanolamide as thickener, curve (b); with 1.0% copra diethanolamide as thickener, curve (c); with 0.5% of 2-hydroxypropyl-isostearylamide as thickener in accordance with this invention, curve (d); and with 1.0% of 2-hydroxypropyl-isostearylamide as thickener in accordance with this invention, curve (e).

The results are set forth in Table II hereafter and in FIG. 3. In FIG. 3, curve (a) corresponds to the viscosities obtained with increasing quantities of NaCl without thickening agents, curve (b) with 0.5% of copra diethanolamide, curve (c) with 1% of copra diethanolamide, curve (d) with 0.5% of the thickening agent from Example 1, and curve (e) with 1% of the thickening agent from Example 1. On these curves, the NaCl content is given on the x-axis and viscosity in mPa.s on the y-axis.

TABLE II

| | Viscosity at 20° C. (mpa · s) | Foaming Power at 0.1% in city water Immediate foam (ml) | Foam after 5 min. (ml) | Cloud Point (°–C.) | Visual at 20°C. |
|---|---|---|---|---|---|
| Without Thickening agent: | | | | | |
| As such | 25 | 370 | 360 | −2 | clear |
| +1.00% NaCl | 75 | | | | clear |
| +2.00% NaCl | 840 | | | | clear |
| +2.50% NaCl | 1100 | 350 | 340 | +14 | clear |
| +3.00% NaCl | 360 | | | | clear |
| 0.5% agent from Example 1: | | | | | |
| As such | 30 | 330 | 320 | −2 | clear |
| +0.50% NaCl | 42 | | | | clear |
| +1.00% NaCl | 210 | | | | clear |
| +1.25% NaCl | 960 | 400 | 380 | −1 | clear |
| +1.50% NaCl | 1600 | | | | clear |
| +1.75% NaCl | 1600 | | | +11 | clear |
| +2.00% NaCl | 750 | | | +18 | cloudy |
| 0.5% copra diethanol-amide: | | | | | |
| As such | 25 | 310 | 300 | −2 | clear |
| +1.00% NaCl | 150 | | | | clear |
| +1.50% NaCl | 980 | | | | clear |
| +1.75% NaCl | 1300 | 360 | 350 | −1 | clear |
| +2.00% NaCl | 1240 | | | | |
| 0.5% copra monoisopro panolamide | | | | | |
| +1.25% NaCl | 380 | | | 0 | |
| +1.50% NaCl | 510 | | | 0 | |
| +1.75% NaCl | 1160 | | | +3 | |
| +2.00% NaCl | 980 | | | +6 | |
| 1% agent from Example 1: | | | | | |
| As such | 30 | 310 | 300 | −2 | clear |
| +0.30% NaCl | 100 | | | | clear |
| +0.75% NaCl | 370 | | | −2 | clear |
| +1.00% NaCl | 2400 | 360 | 350 | +16 | clear |
| +1.25% NaCl | 2000 | | | | turbid |

TABLE II-continued

| | Viscosity at 20° C. (mpa · s) | Foaming Power at 0.1% in city water Immediate foam (ml) | Foam after 5 min. (ml) | Cloud Point (°–C.) | Visual at 20°C. |
|---|---|---|---|---|---|
| 1% copra diethanol-amide | | | | | |
| As such | 25 | 310 | 300 | −2 | clear |
| +1.00% NaCl | 310 | | | | clear |
| +1.50% NaCl | 1450 | | | | clear |
| +1.75% NaCl | 1750 | 380 | 370 | −1 | clear |
| +2.00% NaCl | 900 | | | | |
| 1% copra monoisopro panolamide | | | | | |
| +0.50% NaCl | 75 | | | +2 | |
| +0.75% NaCl | 230 | | | −2 | |
| +1.00% NaCl | 940 | | | −2 | |
| +1.25% NaCl | 1920 | | | −2 | |

Although the present invention has been described with reference to certain preferred embodiments, modifications or changes may be made therein by those skilled in this art. For example, instead of using 2-hydroxypropyl-isostearyl amide as the thickening agent, 2-hydroxyethyl-isostearylamide or 2- or 3-hydroxybutyl-isostearylamide may also be used. All such obvious modifications may be made herein without departing from the scope and spirit of this invention as defined by the appended claims.

What is claimed is:

1. A method for making a beta-hydroxylalkyl-terminally branched fatty acid amide having a maximum color value of 5.0 Gardner units, up to about 5% by weight of esteramide by-products and up to about 1% by weight of free amine content, said method comprising:

heating a quantity of a terminally branched fatty acid in an inert atmosphere to a temperature of between about 40° to about 70° C.;

adding an antioxidant to said heated fatty acid and mixing for a time period of from about 0.5 to about 2.0 hours;

adding a stoichiometric excess amount of a beta-hydroxyalkylamine and adjusting the temperature to between about 90° C. and 110° C.;

adding a minor effective amount of an amidation catalyst to said vessel to form a reaction mixture and increasing the temperature of the reaction mixture to between about 145° to 170° C.;

permitting the amidation reaction to proceed under generally constant temperature and inert atmosphere conditions until an acid index value (mg KOH/g) of less than about 5.0 is obtained;

adding a second quantity of an antioxidant to the reaction vessel and reducing the pressure in said reaction vessel until substantially all excess amine is eliminated from said reaction mixture;

permitting the temperature of the reaction mixture to fall to a temperature of less than about 75° C. while maintaining the inert atmosphere; and thereafter, permitting the beta-hydroxyalkyl-terminally branched fatty acid amide product to cool to room temperatures.

* * * * *